United States Patent
Lenihan et al.

(10) Patent No.: US 9,421,348 B2
(45) Date of Patent: Aug. 23, 2016

(54) SYSTEMS AND METHODS FOR MOVING AND CIRCULATING FLUID TO TREAT ALZHEIMER'S DISEASE

(71) Applicant: ECOLE POLYTECHNIQUE FEDERALE DE LAUSANNE (EPFL), Lausanne (CH)

(72) Inventors: Tim Lenihan, Hradec Kralove (CZ); Bruce Meadows, Gersau (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 0 days.

(21) Appl. No.: 14/503,094

(22) Filed: Sep. 30, 2014

(65) Prior Publication Data

US 2015/0094644 A1    Apr. 2, 2015

Related U.S. Application Data

(60) Provisional application No. 61/885,423, filed on Oct. 1, 2013.

(51) Int. Cl.
*A61M 5/00* (2006.01)
*A61M 27/00* (2006.01)

(52) U.S. Cl.
CPC ..... *A61M 27/006* (2013.01); *A61M 2202/0464* (2013.01)

(58) Field of Classification Search
CPC .......... A61M 27/002; A61M 5/14276; A61M 27/006; A61M 2205/3355; A61M 2205/8287; A61M 2210/1085; A61M 5/1723
USPC ....................................................... 604/8–10
See application file for complete search history.

(56) References Cited

U.S. PATENT DOCUMENTS

| | | | |
|---|---|---|---|
| 4,416,657 A * | 11/1983 | Berglund | A61M 39/0247 604/175 |
| 4,610,658 A * | 9/1986 | Buchwald | A61M 27/002 417/417 |

(Continued)

FOREIGN PATENT DOCUMENTS

| EP | 1 614 442 A2 | 1/2006 |
|---|---|---|
| WO | WO-03/015710 A2 | 2/2003 |
| WO | WO-2011/114260 A1 | 9/2011 |

OTHER PUBLICATIONS

Adams et al., "Disturbances of Cerebrospinal Fluid Circulation, Including Hydrocephalus and Meningeal Reactions," Principles of Neurology, (1989), 30:501-515.

(Continued)

*Primary Examiner* — Philip R Wiest
(74) *Attorney, Agent, or Firm* — Foley & Lardner LLP; Christopher C. Bolten; Nicola A. Pisano

(57) ABSTRACT

A system for the treatment of Alzheimer's disease is provided by moving cerebrospinal fluid containing particles know to contribute to onset of Alzheimer's disease from a source of cerebrospinal fluid to the stomach or bladder, where the particles are safely digested by gastric acid or excreted, the system including an implantable pump, an inlet catheter, an outlet catheter, and a one-way valve. The system further includes at least one filter to filter harmful particles from the cerebrospinal fluid and return the filtered cerebrospinal fluid back to the source of cerebrospinal fluid, where the harmful particles blocked by the filter may be rinsed off the filter and transported to the stomach or bladder.

20 Claims, 9 Drawing Sheets

(56) References Cited

U.S. PATENT DOCUMENTS

| | | | |
|---|---|---|---|
| 4,857,046 | A | 8/1989 | Stevens et al. |
| 4,950,232 | A | 8/1990 | Ruzicka et al. |
| 5,334,315 | A | 8/1994 | Matkovich et al. |
| 5,372,573 | A | 12/1994 | Habib |
| 5,385,541 | A | 1/1995 | Kirsch et al. |
| 5,385,582 | A | 1/1995 | Ommaya |
| 5,980,480 | A | 11/1999 | Rubenstein et al. |
| 7,025,742 | B2 * | 4/2006 | Rubenstein ......... A61M 1/1003 604/8 |
| 7,335,179 | B2 | 2/2008 | Burnett |
| 7,909,790 | B2 | 3/2011 | Burnett |
| 8,202,248 | B2 | 6/2012 | Burnett et al. |
| 8,398,577 | B2 | 3/2013 | Burnett |
| 8,585,635 | B2 * | 11/2013 | Degen ................. A61M 1/1676 604/29 |
| 2009/0131850 | A1 | 5/2009 | Geiger |
| 2012/0209165 | A1 | 8/2012 | Degen et al. |

OTHER PUBLICATIONS

Aria et al., "Tau in cerebrospinal fluid: a potential diagnostic marker in Alzheimer's disease," Ann. Neurology, (1995), 38(4):649-652.

Bush et al., "Beta A4 amyloid protein and its precursor in Alzheimer's disease," Pharmac. Tera., (1992), 56(1):97-117.

Chen et al., "Effectiveness of shunting in patients with normal pressure hydrocephalus predicted by temporary, controlled-resistance, continuous lumbar drainage: a pilot study," J. Neurol. Neurosurg. Psychiatry, (1994), 51:1430-1432.

Martinez et al., "Relationship of interleukin-1 beta and beta 2-microglobulin with neuropeptides in cerebrospinal fluid of patients with dementia of the Alzheimer type," J. Neuroimmunol., (1993), 48(2):235-240.

Nakamura et al., "Amyloid beta protein levels in cerebrospinal fluid are elevated in early-onset Alzheimer's disease," Ann. Neurology, (1994), 36:(6):903-911.

Ono et al., "Formation of amyloid-like substance from beta-2-microglobulin in vitro. Role of serum amyloid P component: a preliminary study," Nephron, (1994), 66:404-407.

Silverberg et al., "Alzheimer's disease, normal-pressure hydrocephalus, and senescent changes in CSF circulatory physiology: a hypothesis," Lancet Neurol., (2003), 2(8):506-511.

International Search Report and Written Opinion dated Mar. 24, 2015 in International PCT Patent Application No. PCT/IB2014/002771.

* cited by examiner

SYSTEMS AND METHODS FOR MOVING AND CIRCULATING FLUID TO TREAT ALZHEIMER'S DISEASE

CROSS-REFERENCE TO RELATED APPLICATIONS

This application claims the benefit of priority of U.S. Provisional Application No. 61/885,423, filed Oct. 1, 2013, the entire contents of which are incorporated herein by reference.

FIELD OF THE INVENTION

The present application relates generally to the field of medical devices. More particularly, it relates to implantable, pump-assisted drainage devices, capable of draining fluid (e.g. cerebrospinal fluid) from one bodily cavity into another bodily cavity, or from one bodily cavity into the same bodily cavity after treating the fluid.

BACKGROUND OF THE INVENTION

There are a variety of conditions which result in pathologic chronic collection of bodily fluids within the body of a person or where the removal of certain bodily fluids may be desirable. In particular, it may be desirable to remove cerebrospinal fluid (CSF) from certain patients with Alzheimer's disease, thereby eliminating or reducing the concentration of certain particles, such as beta amyloid (BA) and tau.

The brain and spinal cord are encased within the cranium and vertebral column inside a thin membrane known as the arachnoid. The volume of the intracranial space is on average about 1700 mL. The volume of the brain is approximately 1400 mL; the volume of the intracranial blood is approximately 150 ml; the remaining 150 mL is filled with CSF. The CSF circulates within the subarachnoid space. It is formed principally by the choroid plexuses, which secrete about 80% of the total volume. The sources of the remainder are the vasculature of the subependymal regions, and the pia mater. The total volume of the CSF is renewed several times per day, so that about 500 mL are produced every 24 hours.

The CSF is absorbed through the arachnoid villi, located principally over the superior surfaces of the cerebral hemispheres. Some villi also exist at the base of the brain and along the roots of the spinal nerves. The absorptive processes include bulk transport of large molecules and diffusion across porous membranes of small molecules. See, e.g., Adams et al., (1989) "Principles of Neurology," pp. 501-502.

The principle on which this invention is based is that in some persons with Alzheimer's disease there is dysfunction of the CSF resorptive mechanism, leading to the retention in the CSF of substances which result in histologic lesions associated with adult-onset dementia of the Alzheimer's type, or which are neurotoxic, or both.

There are several examples of low-molecular weight proteins or peptides that are known to be present in elevated concentrations in the CSF of persons suffering from adult-onset dementia of the Alzheimer's type. For example, elevated levels of BA have been found in the CSF of patients with early-onset Alzheimer's disease. See, Nakamura et al., (1994) "Amyloid beta protein levels in cerebrospinal fluid are elevated in early-onset Alzheimer's disease," Ann. Neurology 36: 903-911. BA is known to self-aggregate into molecules of amyloid of the type that typify the core plaques found in the brain in persons suffering from adult-onset dementia of the Alzheimer's type. In fact, BA deposition in the brain is the only microscopic lesion specific for Alzheimer's disease. Furthermore, BA has been shown to be neurotoxic, as described in Bush et al., (1992) "Beta A-4 amyloid protein and its precursor in Alzheimer's disease," Pharmac. Tera. 56: 97-117. BA is also a component of microscopic cerebral lesions known as neurofibrillary tangles, characteristically found in adult-onset dementia of the Alzheimer's type.

Beta-2 microglobulin is another example of a low-molecular-weight protein whose concentration in the CSF increases with age and reaches high levels in patients with adult-onset dementia of the Alzheimer's type, as reported in Martinez et al., (1993) "Relationship of interleukin-1 beta and beta.sub.2-microglobulin with neuropeptides in cerebrospinal fluid of patients with dementia of the Alzheimer type," J. Neuroimmunology 48: 235-240. Beta-2 microglobulin is associated with amyloid deposits in some tissues of patients on long-term renal hemodialysis. See, Ono et al., (1994) "Formation of amyloid-like substance from beta-2-microglobulin in vitro. Role of serum amyloid P component: a preliminary study," Nephron 66: 404-407.

Another substance that accumulates in the CSF in patients with adult-onset dementia of the Alzheimer's type is tau, a component of the neurofibrillary tangles found in involved brain tissue. Tau concentrations in CSF are regularly increased in this syndrome with eight fold increases present in half of the patients, as reported in Arai et al., (1995) "Tau in cerebrospinal fluid: a potential diagnostic marker," Ann. Neurology 38: 649-52.

Researchers have also discovered that oligomeric assemblies of beta amyloid peptides of 42 amino acids (Aβ42) are the probable source of cellular toxicity in human brains. Aβ42 is a major constituent of plaque and vessel amyloid in Alzheimer's disease. Aβ42 has been suggested to promote tau phosphorylation and toxicity in Alzheimer's disease pathogenesis. The dimer, trimer, and tetramer forms of oligomers, which have molecular weights from 4 to 60 kDa, are probably the most toxic oligomers. Therefore, it is desirable to remove these particular particles from the CSF.

Previously-known devices have attempted to use filtration techniques to remove or reduce concentrations of harmful proteins from patient body fluids. For example, Matkovich, U.S. Pat. No. 5,334,315 describes a method and device that can be used to remove a body fluid from a patient, treat that fluid to remove an undesirable component, and return the fluid to the patient. That patent includes a partial list of the types of deleterious or undesirable substances that may be removed from a fluid, such as proteins, polypeptides, interleukins, immunoglobulins, proteases and interferon. The fluids from which these substances may be removed are described as including CSF, blood, urine and saliva. However, Matkovich does not suggest that his method and device could be used to treat patients suffering from adult-onset dementia of the Alzheimer's type.

Kirsch et al., U.S. Pat. No. 5,385,541 describes a CSF shunt mechanism used to treat hydrocephalus by draining CSF into the patient's abdomen, chest or vascular system. The system may include a one-way valve to prevent backflow. Kirsh does not describe the use of such a system to treat adult-onset dementia of the Alzheimer's type, however. Likewise, Ruzicka et al., U.S. Pat. No. 4,950,232 discloses another CSF shunt system, but again does not suggest the possible applicability of using such a shunt to treat adult-onset dementia of the Alzheimer's type.

Chen et al., (1994) "Effectiveness of Shunting in patients with normal pressure hydrocephalus predicted by temporary, controlled-resistance, continuous lumbar drainage: a pilot study," J. Neurol. Neurosurg. Psychiatry 51:1430-1432, describes use of a "silicon" catheter for draining CSF from the subarachnoid region into an external collection bag.

It has been theorized that the removal of the proteins BA and tau from the CSF in the brain may slow the advance of Alzheimer's disease. Previous attempts to use a standard shunt, like a hydrocephalus shunt, to move CSF from the brain to the abdomen have failed since the deleterious proteins were believed to have found their way back to the brain. Other attempts to remove proteins within the CSF include drugs, which result in undesirable side effects.

It would be desirable to provide methods and apparatus to reduce the concentration of proteins BA and tau within the CSF in the brain.

More specifically, it would be desirable to provide methods and apparatus to remove the harmful particles from the CSF in the brain and prevent the particles from moving or migrating back into the brain.

As described above, the total volume of CSF is renewed several times per day. The continual turnover of CSF is considered to play a key role in the clearance of toxic particles, such as BA and tau. CSF turnover is directly proportional to CSF formation rate and inversely related to the volume of the CSF space.

It is believed that in some persons with Alzheimer's disease, there is a trend towards lower CSF production, hence a decrease in CSF turnover, and greater resistance to CSF outflow. See, Silverberg et al., (2003) "Alzheimer's disease, normal-pressure hydrocephalus, and senescent changes in CSF circulatory physiology: a hypothesis," Lancet Neurol 2(8): 506-511.

Therefore, it further would be desirable to provide methods and apparatus to replenish the volume of CSF in the cerebral ventricle after the removal of CSF to enhance CSF turnover and reduce BA and tau concentrations in the brain.

SUMMARY OF THE INVENTION

The present invention overcomes the drawbacks of previously-known systems for treating Alzheimer's disease and dementia by providing a fluid removal system and methods of use that reduce the concentration of or eliminate BA and tau from the CSF by removing CSF from the brain and preventing harmful particles from migrating back to the brain. In particular, it is believed that by transporting harmful particles to the stomach, those particles may be digested by the hydrochloric acid found in gastric acid, thereby ridding the body of such particles and preventing them from migrating to the brain. Alternatively, the CSF may be transported to the bladder, where it may be excreted.

Additionally, the present disclosure overcomes drawbacks of previously-known systems for treating Alzheimer's disease and dementia by providing a fluid replenishment system, and methods of use, that reduce the concentration of or eliminate BA and tau from CSF by delivering filtered CSF with the harmful particles removed to the subarachnoid region and replenishing depleted CSF subsequent to draining to enhance CSF turnover. In particular, it is believed that by draining CSF in patients with Alzheimer's disease, at least some of the CSF must be replaced to enhance CSF turnover. By delivering filtered CSF back to the brain of patients with Alzheimer's disease, CSF turnover may be enhanced.

In accordance with one aspect of the present invention, the system preferably comprises an implantable pump, an inlet catheter, an outlet catheter, and a one-way valve. The inlet catheter is configured to connect the CSF within a cerebral ventricle of a patient to the pump. The outlet catheter is configured to connect the pump to the stomach or bladder of the patient. The pump, which in a preferred embodiment may be a positive displacement gear pump, may be located in the chest or abdomen of the patient, and is configured to transfer fluid from the inlet catheter to the outlet catheter. The one-way valve is configured to permit CSF to flow in one direction: away from the inlet catheter and towards the stomach or bladder. The inlet and outlet catheters may be sealed to the cerebral ventricle and/or stomach or bladder wall with a flange.

In accordance with another aspect of the present invention, the system preferably comprises an implantable pump, a valve for directing the CSF fluid, an inlet catheter, a return catheter, an outlet catheter, a fine filter, and a CSF reservoir. The inlet catheter is configured to connect the CSF within a cerebral ventricle of a patient to the pump. The return catheter is configured to connect the fine filter to the cerebral ventricles or spine of the patient. The outlet catheter is configured to connect the fine filter to the stomach or bladder of the patient. The inlet, return, and outlet catheters may be sealed to the cerebral ventricle and/or stomach or bladder wall with a flange. The pump, which in a preferred embodiment may be a positive displacement gear pump, may be located in the chest or abdomen of the patient, and is configured to transfer fluid from the inlet catheter to the return catheter or the outlet catheter. The valve is configured to direct the CSF towards the fine filter or the CSF reservoir. The fine filter is configured to trap the harmful particles in the CSF and transport the filtered CSF to the return catheter. The CSF reservoir stores CSF, which is used to wash the trapped particles off the fine filter and carry them to the stomach or bladder of the patient.

In accordance with another aspect of the present invention, the system may comprise a coarse filter in series with the fine filter such that particles of different sizes may be separated and processed differently. For example, particles with molecular weights between 4 kDa and 60 kDa may be blocked and transported to the stomach or bladder of the patient, while other particles, which are not harmful or toxic, are allowed to return to the CSF in the brain.

In accordance with another aspect of the present invention, the system may comprise a bacterial filter on or within the outlet catheter, which is configured to prevent bacteria from passing backward through the system to the brain. The bacterial filter may comprise an ultraviolet light module configured to irradiate fluid passing through the outlet catheter. Alternatively, some or all of the system components may be coated with or impregnated with antibiotic or antimicrobial coatings or deposits to prevent infection.

In some embodiments, the system may include a microcontroller for controlling the operation of the pump and the microcontroller may be responsive to a pressure sensor and/or a clock. The pressure sensor may provide information regarding the pressure of the CSF within the cerebral ventricle, the filter, or the catheters. In this manner, the microcontroller may be programmed to pump CSF from the cerebral ventricle to the stomach or bladder only when the pressure of the CSF exceeds a predetermined value. Alternatively, the microcontroller may be programmed to pump the CSF in predetermined volumes or at predetermined intervals, which may be titrated for each patient. Alternatively, the microcontroller may be programmed to activate the valve to change the direction of the CSF flow in response to outputs of the sensors.

The implantable device may include a rechargeable power source, such as a battery. In accordance with another aspect of the present invention, the system may include an extracorporeal controller configured to transmit energy to the implantable components, communicate information to the implantable components, and/or receive data from the implantable components.

Methods of reducing the concentration of particles known to contribute to Alzheimer's disease from a patient's CSF fluid also are provided.

BRIEF DESCRIPTION OF THE DRAWINGS

These and other features, aspects, and advantages of the present invention will become apparent from the following description, appended claims, and the accompanying exemplary embodiments shown in the drawings, which are briefly described below.

DETAILED DESCRIPTION OF THE PREFERRED EMBODIMENTS

Figure 1A:
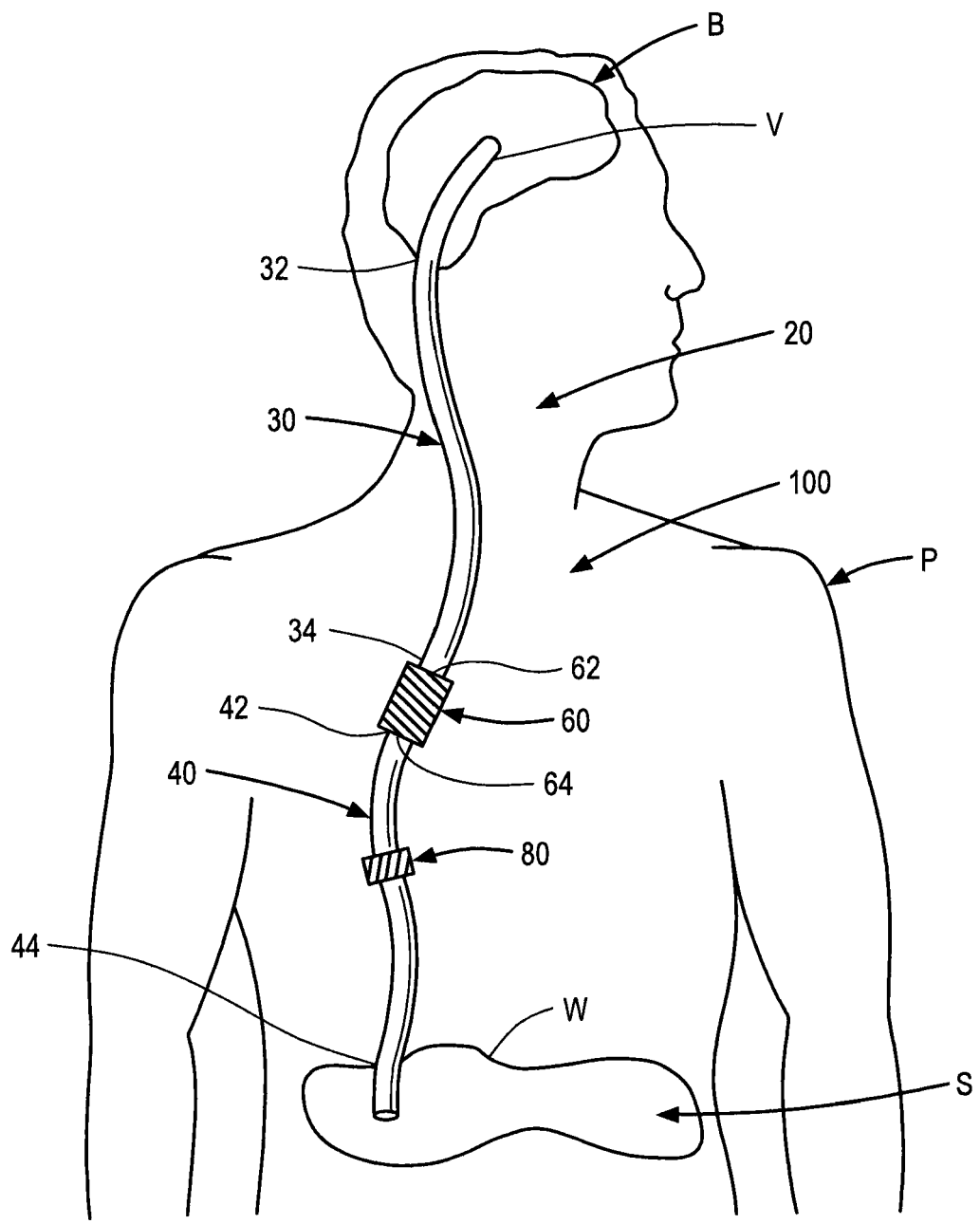
FIGS. 1A and 1B are, respectively, schematic views of exemplary embodiments of the fluid removal system of the present invention implanted within a patient.

The system of the present invention comprises devices and methods for facilitating the removal of harmful particles within the CSF fluid from the cerebral ventricles and augmenting the rate of CSF turnover to treat a neurodegenerative disorder such as Alzheimer's disease. More specifically, the apparatus and methods described herein are designed to treat Alzheimer's disease and reduce the concentration of harmful particles within the CSF by transporting the CSF to the stomach for digestion and/or bladder for excretion. The natural acids in the stomach are expected to digest the harmful particles (including BA and tau) within the CSF and the residue is expected to be excreted through the digestive system or gastro-intestinal system. Alternatively, the CSF may be pumped directly to the bladder, where it may be excreted. Additionally, the apparatus and methods described herein are designed to filter the CSF from the brain, circulate the filtered CSF back to the cerebral ventricle or the spine, and transport the harmful particles to the stomach or bladder. By returning the filtered CSF with the harmful particles removed back to the subarachnoid region, the filtered CSF will replenish depleted CSF subsequent to draining.

A patient's CSF is at least partially replaced every day. By removing a portion of a patient's CSF with the present invention on a continual or episodic basis, the patient's brain will be replenished with fresh CSF. The addition of fresh CSF may also dilute the remaining concentrations of deleterious materials (such as neurotoxic substances, substances associated with histologic lesions or certain particles, like BA or tau proteins) in the patient's CSF, thereby treating the patient for Alzheimer's disease and slowing the advance of the symptoms of Alzheimer's disease. It is also contemplated that by reducing the concentrations of BA and tau within the patient's CSF, the present invention may promote dissolution of existing plaques, and thereby reverse the patient's trend toward increasing mental deficit.

However, for patients with Alzheimer's disease, CSF formation does not allow for natural replenishing of fresh CSF. In addition, the flow rate of CSF pumped out of the brain may not be sufficient to clear enough BA from the brain to prevent the plaque accumulation or promote the dissolution of existing plaques. Thus, it is desirable to increase the flow rate of the CSF pumped out of the brain. However, increasing the flow rate of the CSF pumped out of the brain will reduce the volume and the pressure of the CSF in the brain. It is desirable to keep the volume or pressure of the CSF in the brain at a stable level. Thus, it is desirable to replenish the volume of the CSF through unnatural mechanisms after the drainage of the CSF.

The present invention, in some embodiments, provides a system that may increase the flow rate of the CSF pumped out of the brain, remove the toxic particles from the CSF through filtering, and replenish the volume of the CSF in the brain by circulating the filtered CSF that has the toxic particles removed back to the brain or spine of the patient. Only the toxic particles are transported to the stomach or bladder of the patient.

Figure 1B:
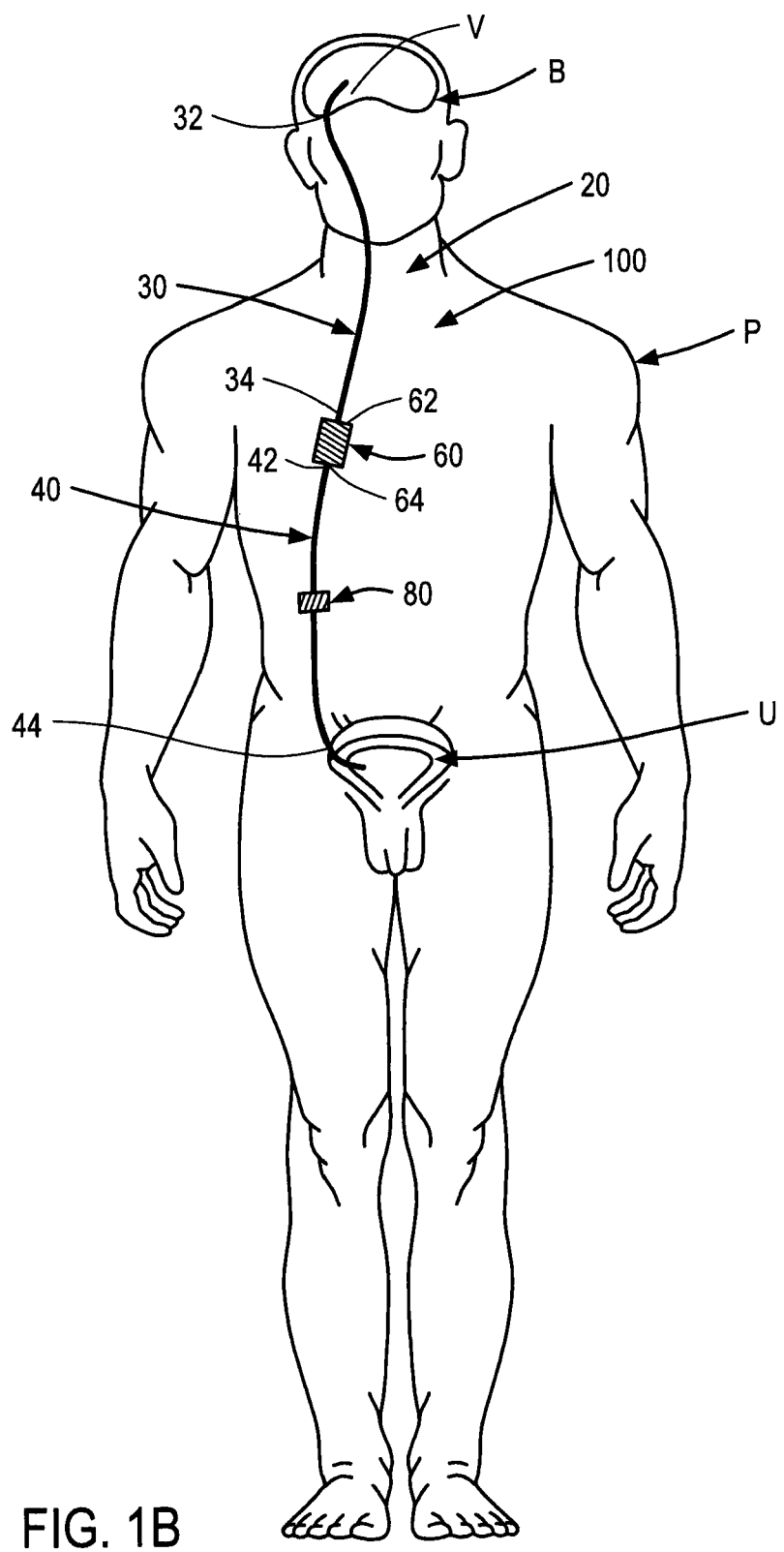
Figure 2:
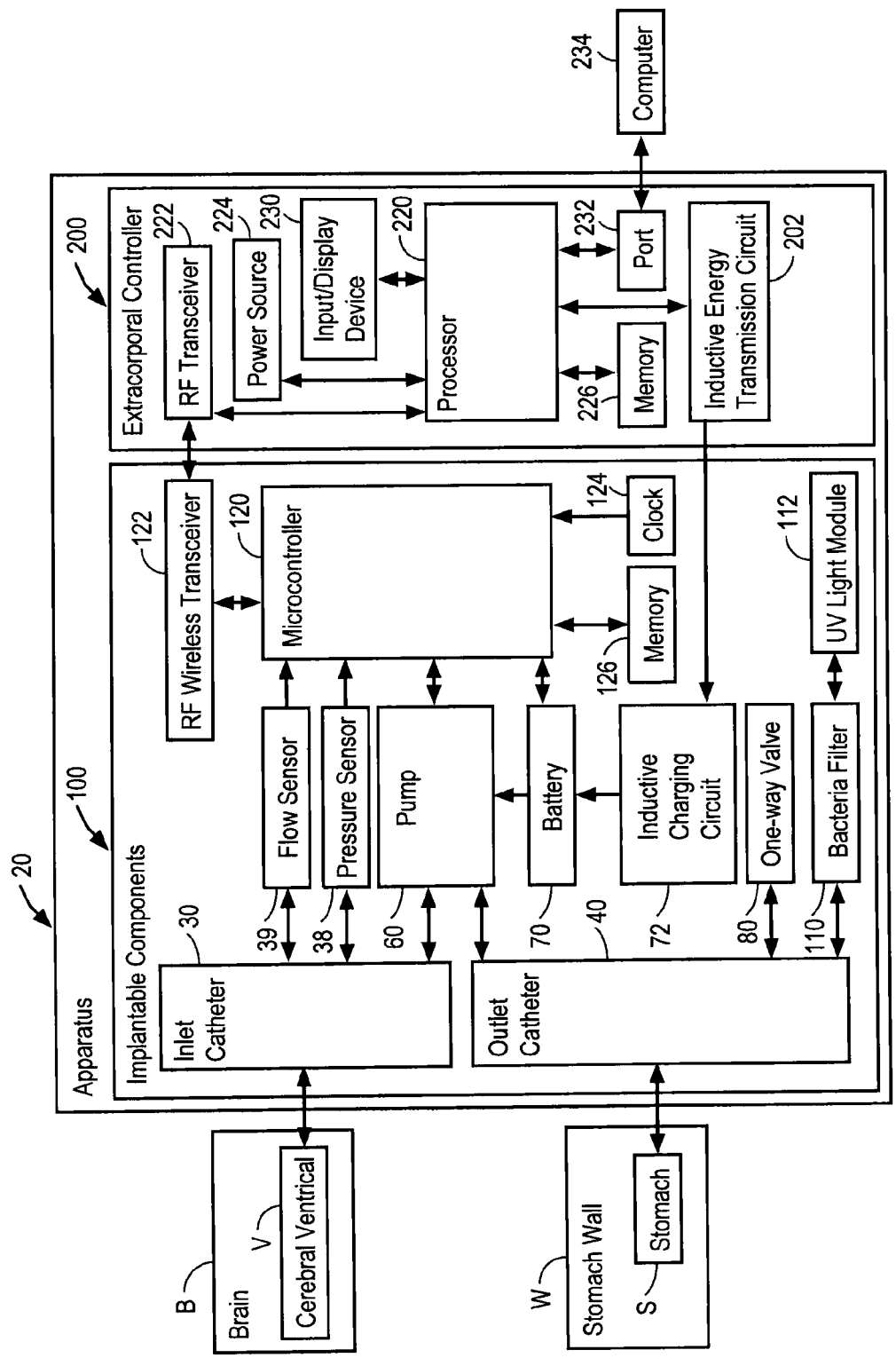
FIG. 2 is a schematic diagram of a fluid removal system of the present invention.

As shown in FIGS. 1A, 1B and 2, exemplary embodiment of system 20 constructed in accordance with the principles of the present invention comprises implantable components 100 including inlet catheter 30 connecting cerebral ventricle V of brain B of a patient P to implantable pump 60, and outlet catheter 40 connecting pump 60 to stomach S of the patient. Alternatively, the outlet end of outlet catheter 40 may be coupled to the patient's urinary bladder U, as depicted in FIG. 1B. System 20 provides a unidirectional path for movement of CSF fluid to flow from brain B to stomach S or bladder U. Fluid from the cerebral ventricle is drawn into a proximal end of inlet catheter 30 by pump 60, and expelled through outlet catheter 40 through stomach wall W into the stomach. One-way valve 80 is positioned along outlet catheter 40 to prevent back flow of fluid through system 20. Optional bacterial filter 110 also may be positioned along outlet catheter 40, inlet catheter 30, or disposed within the housing of pump 60 to destroy harmful bacteria and prevent bacteria from migrating through system 20 to brain B. Alternatively, or in addition, the components of system 20 may be coated or impregnated with an antibacterial or antimicrobial coating to reduce the risk of infection.

In a preferred embodiment, inlet catheter 30, outlet catheter 40 and pump 60 are implanted separately and then coupled together during implantation of pump 60. For example, catheters 30 and 40 may be separately implanted using a tunneling technique to place an inlet end of catheter 30 in communication with a source of CSF, and to place an outlet end of catheter 40 in communication with the stomach or the bladder. The outlet end of catheter 30 and the inlet end of catheter 40 then may be lead to the site for implantation of pump 60, and coupled to the pump prior to the implantation of pump 60. As will be understood, components 30 and 40 comprise biocompatible materials, and may be provided in standard lengths or a single length that may be cut to size to fit a particular patient's anatomy during the implantation procedure. Each connection in system 20 preferably includes a fluid-tight seal and may be accomplished through any variety of methods known to one of skill in the art.

Inlet catheter 30 and outlet catheter 40 may be formed from a resilient material, such as implant grade silicone or reinforced silicone tubing. The catheters may be reinforced along a portion of their length or along the entire length of the catheters. Reinforcement of the tubing may be accomplished via ribbon or wire braiding or lengths of wire or ribbon embedded or integrated within or along the tubing. The braiding or wire may be fabricated from metals such as stainless steels, superelastic metals such as nitinol, or from a variety of suitable polymers.

Inlet catheter 30 has inlet end 32 and outlet end 34. Inlet end 32 is configured to be disposed in fluid communication with a source of CSF fluid. For example, inlet end 32 may be positioned within the CSF of a cerebral ventricle of the brain of patient P. More specifically, inlet end 32 may be positioned within the arachnoid membrane, the subarachnoid space, or one of the lateral ventricles. The ventricles form a group of interconnected cavities that are located within the cerebral hemispheres and brain stem. These ventricles or spaces are continuous with the central canal of the spinal cord and are similarly filled with CSF that may be removed by system 20 and replenished by the body of the patient.

Inlet end 32 may be configured in any form suitable for placement within brain B so that it is capable of collecting CSF from a cerebral ventricle. Conveniently, the form of inlet end 32 may be similar or identical to conventional ventricular catheters of the type used for draining CSF for treating hydrocephalus, such as those described in U.S. Pat. Nos. 5,385,541 and 4,950,232, the full disclosures of which are incorporated herein by reference. Suitable ventricular catheters that may be incorporated into systems constructed according to the present invention are available from commercial suppliers, such as Medtronic PS Medical, Goleta, Calif.

Figure 3:
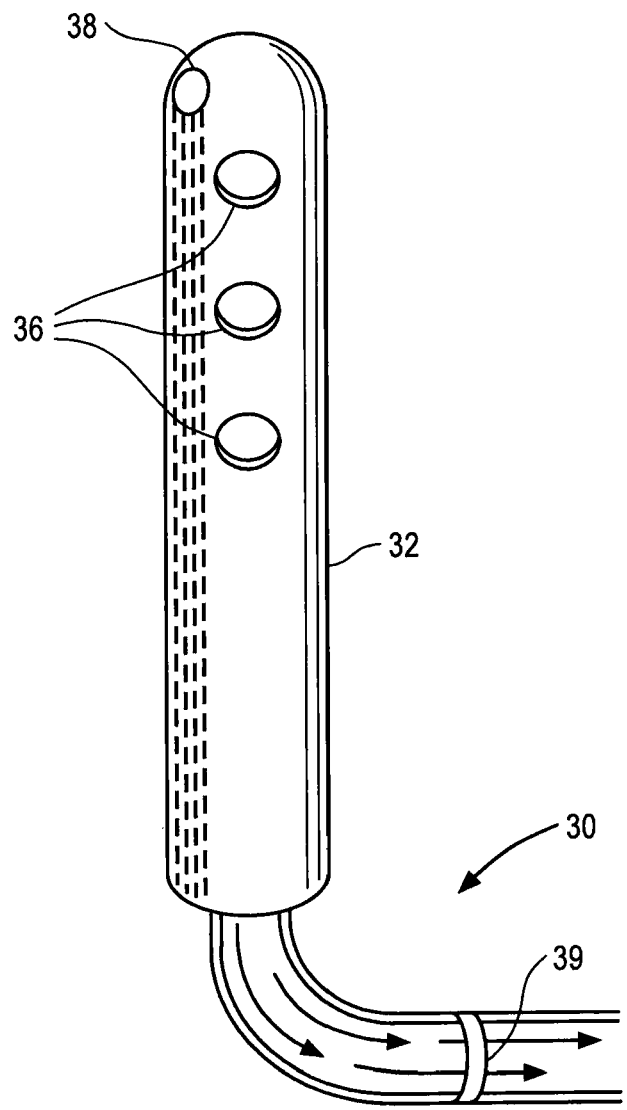
FIG. 3 is a perspective view of the inlet end of the inlet catheter of the fluid removal system.

Referring to FIG. 3, one example of inlet end 32 of inlet catheter 30 is described. Inlet end 32 may include multiple perforations or holes 36, which preferably do not extend more than about 1 to 1.5 cm from the tip. Although a particular inlet hole arrangement is shown, other arrangements may be used without departing from the scope of the invention. Inlet end 32 preferably comprises biocompatible material suitable for implantation in the patient such as implant grade low bending modulus material that is generally kink resistant, such as silicone or reinforced silicone, or medical shunt tubing. The tubing may have an outer diameter of about 2.0 mm and an inner diameter of about 0.5-1.5 mm. Inlet end 32 further may comprise a flange configured to promote sealing to the brain, to allow inlet catheter 30 to pass into the brain without fluid leakage.

One or more sensors may be integrated into system 20 for detecting and/or indicating a variety of fluid and/or pump parameters to other components of system 20 or to the physician or patient. For example, inlet end 32 further may include, or be in communication with, pressure sensor 38, such as a pressure transducer, configured to monitor the CSF pressure at inlet end 32 of inlet catheter 30, as shown in FIG. 3. Pressure sensor 38 may be disposed in the CSF within the cerebral ventricle V of the brain B and located in the vicinity of the tip of inlet end 32 of inlet catheter 30. Pressure sensor 38 may be used to monitor the intracranial pressure and ensure that the intracranial pressure is not reduced to a level that increases the risk of subdural hematomas or ventricular collapse and midline shifts or that destabilizes the pressure in the ventricles.

Referring now also to FIG. 2, pressure sensor 38 further may be configured to provide an output that is used to control operation of pump 60. For example, pressure sensor 38 may be configured to send a signal to microcontroller 120, in response to sensing a pressure above or below a certain threshold or predetermined level. Microcontroller 120 may be configured to control the operation of pump 60 (as shown in FIG. 2) by activating or stopping the pump in response to the output of pressure sensor 38. More specifically, microcontroller 120 may stop pump 60 when the CSF pressure reaches a minimum pressure value of 6 cm $H_2O$ (generally, CSF removal may be undesirable at fluid pressures below about 6 cm $H_2O$).

Inlet catheter 30 further may include flow sensor 39 to detect, measure, and/or monitor the volume and flow rate of CSF pumped out of the brain. Flow sensor 39 also may be configured to send a signal to microcontroller 120 regarding the volume and flow rate in order to control pump 60. Flow sensor 39 also may be used to ensure that system 20 is operating properly after implantation and during use.

In a preferred embodiment, microcontroller 120 coordinates and controls operation of the components of system 20. For example, microcontroller 120 may use output signals from pressure sensor 38 and flow sensor 39 to control pump 60 by turning the pump on or off or increasing or decreasing the pump speed (and therefore the fluid flow rate). As a further example, the microcontroller may turn off pump 60 when a specific volume of CSF has been pumped from the brain, unless the CSF pressure is more than a threshold value. Microcontroller 120 may be configured to send a signal to a power source coupled to pump 60 to indicate when to provide or stop power to pump 60 responsive to output signals from pressure sensor 38 and/or flow sensor 39. Leads, for example, may be used within system 20 to send signals between the components, such as pressure sensor 38, flow sensor 39, pump 60, and microcontroller 120. Microcontroller 120 further may include memory 126 to record operation of system 20 and/or record a specific algorithm used to drain the CSF.

Figure 4A:
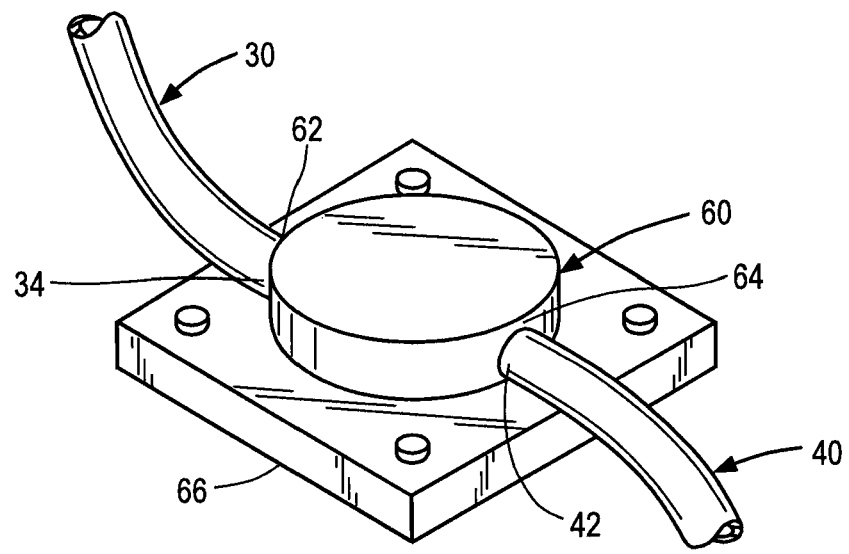
FIGS. 4A and 4B are, respectively, a perspective view of the implantable pump for use in the fluid removal system and a cross-sectional view of an implantable pump mechanism for use within the fluid removal system.

As shown in FIG. 4A, outlet end 34 of inlet catheter 30 is connected to, or coupled with inlet port 62 of pump 60. Outlet port 64 of pump 60 then is connected to proximal end 42 of outlet catheter 40. Pump 60 is configured to control the flow rate and the removal rate of the fluid (e.g. CSF) being removed by the system. More specifically, pump 60 controls the flow rate from the brain through inlet catheter 30 and into outlet catheter 40.

FIG. 4A shows an embodiment of implantable pump 60 connected to inlet catheter 30 and outlet catheter 40. Pump 60 preferably comprises a battery-powered electromechanical pump. Further, pump 60 may be a positive displacement gear pump as described in US Patent Application Publication No. US 2012/0209165 A1, the entirety of the disclosure of which is incorporated herein by reference. Alternatively, pump 60 may be a diaphragm pump, piston pump, rotary pump, peristaltic pump, screw pump, or any other suitable pump configuration. Pump 60 also may be remotely operated as is known in the art.

Figure 4B:
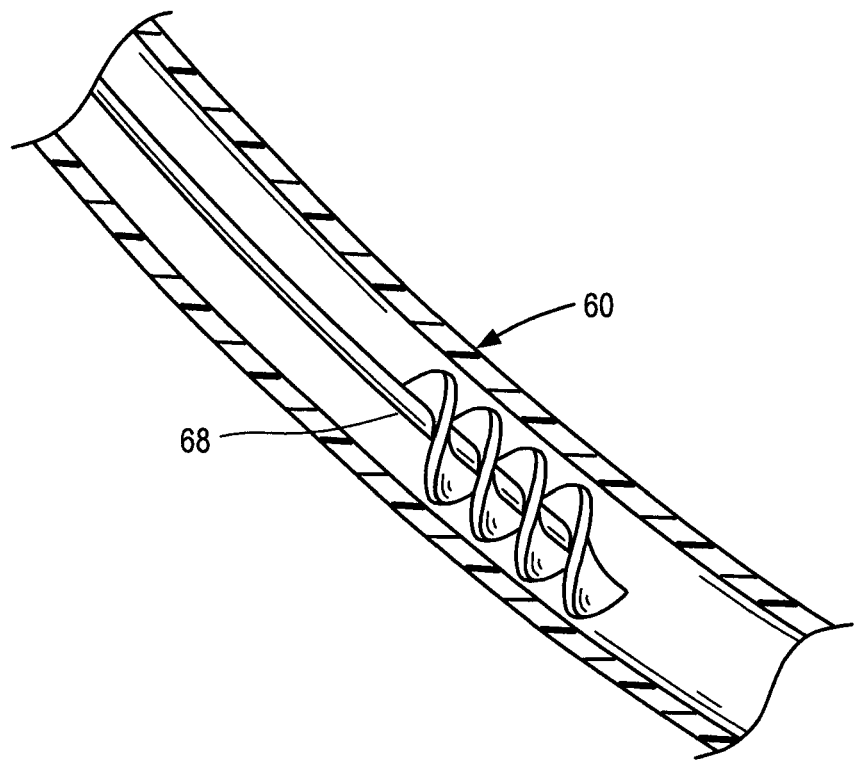

Pump 60 preferably is disposed in a housing manufactured from a suitable biocompatible material, and may include base 66 having suture holes that permit the pump to be fixed to a portion of the patient's anatomy, e.g., within the thorax or peritoneum. FIG. 4B illustrates an alternative screw pump arrangement, suitable for use in system 20, where screw shaft 68 is mounted for rotation within pump 60 and the drive is disposed in a hermetically sealed package mounted to the conduit exterior. The drive may be coupled to the screw shaft 68 with a gear transmission as would be apparent to one of ordinary skill in the art. Other screw pump configurations also may be useful, such as those disclosed in U.S. Pat. No. 4,857,046 to Stevens et al. or U.S. Pat. No. 5,372,573 to Habib.

Pump 60 may be placed and secured anywhere between inlet catheter 30 and outlet catheter 40, although it is preferably implanted at site that provides good accessibility to the surgeon and provides some protection for the device, once implanted. For example, pump 60 may be implanted within the chest or abdomen of the patient. More specifically, pump 60 may be placed in the thoracic cavity and positioned in the lateral mid-thorax near the axillary line and on the under surface of a rib, and may be held in place with sutures to the periosteum.

Referring now to FIG. 2, pump 60 in a preferred embodiment is controlled by microcontroller 120. Pump 60 may operate continuously or periodically to remove CSF from the brain. For example, pump 60 may operate according to a schedule, time, or program, operate on demand, or operate according to the sensed parameters, such as the CSF pressure or the volume pumped. Microcontroller 120 may use the outputs of pressure sensor 38 and/or flow sensor 39 to control the flow rate provided by pump 60, as discussed previously. Alternatively or additionally, pump 60 may maintain a drainage rate of CSF at a rate selected to be equal to the natural daily production of CSF by the patient to allow the body to sufficiently replenish the CSF and maintain an adequate intracranial pressure. Pump 60 may maintain a drainage rate of the fluid in the range of 0.2 ml/min to 0.42 ml/min or 0.42 ml/min to 0.7 ml/min. Alternatively, the pump may be configured to maintain a higher drainage rate, such as 0.7 ml/min (1 L/day) to 1.04 ml/min (1.5 L/day).

Microcontroller 120 may include clock 124 to control pump 60. For example, microcontroller 120 may be programmed to activate the pump periodically in response to clock 124 and to pump a predetermined amount of CSF from the cerebral ventricle V to stomach S accordingly. The predetermined amount may be based on average or specific CSF drainage rates with respect to particular times of day, or may be specifically titrated for a particular patient.

As depicted in FIGS. 1A, 1B, 2, and 6, outlet catheter 40, which may be similar in design to inlet catheter 30, connects pump 60 to the stomach S or bladder U. In particular, inlet end 42 of outlet catheter 40 is coupled with outlet port 64 of pump 60.

Outlet end 44 of outlet catheter 40 is configured to be disposed through stomach wall W of stomach S of the patient, so that CSF is discharged through outlet end 44 into the stomach. Outlet end 44 may comprise a flange configured to promote sealing to the stomach wall, thereby allowing outlet catheter 40 to pass through the stomach wall to prevent fluid leakage. Alternatively, outlet end 44 may be coupled to urinary bladder U, as depicted in FIG. 1B.

Figure 5A:
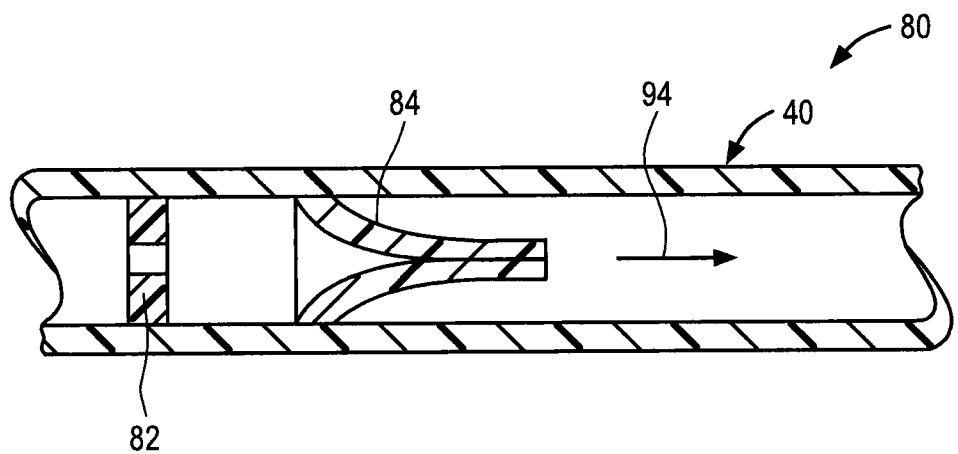
FIGS. 5A, 5B, and 5C illustrate schematic views of alternative one-way valves to control the direction of fluid flow within the fluid removal system.
Figure 5B:
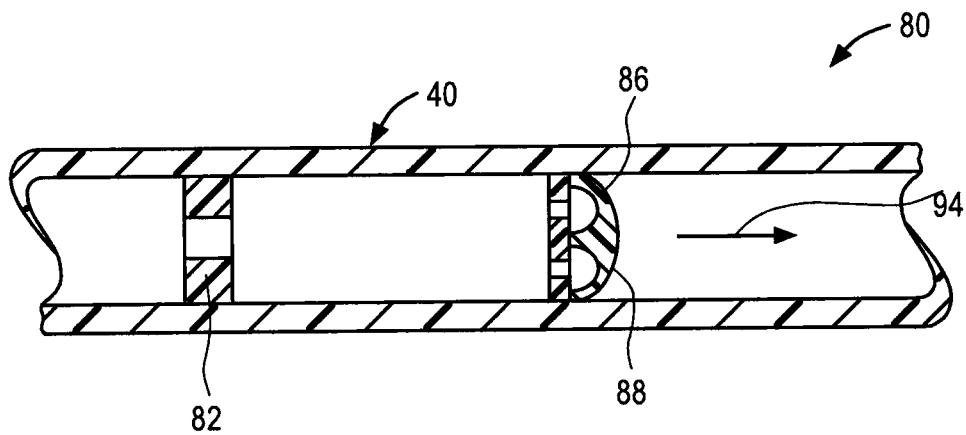
Figure 5C:
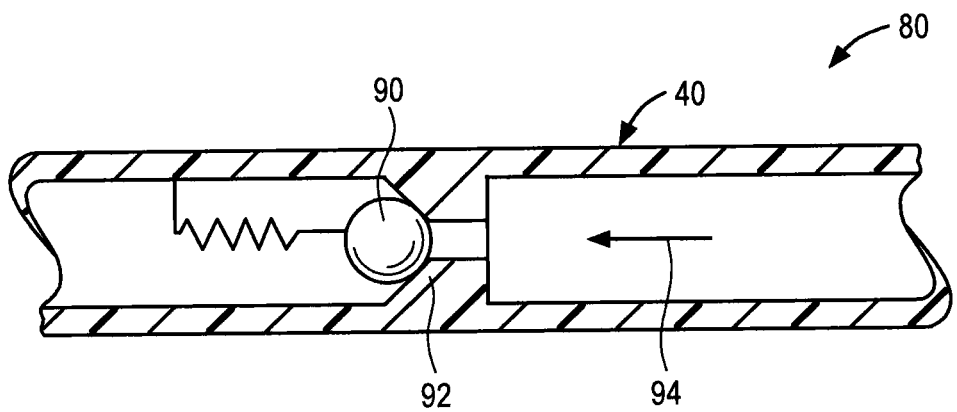

One-way valve 80 may be positioned along outlet catheter 40 to provide unidirectional flow of CSF within system 20. More specifically, one-way valve 80 allows the fluid to flow in only one direction: from the brain to the stomach or bladder. This prevents any backflow to the brain of fluid, such as gastric juices or harmful bacteria from the stomach (or urine from the bladder). One-way valve 80 may be located within or on outlet catheter 40 or more preferably, may be housed within pump 60. Examples of one-way valves 80 suitable for use in system 20 are shown in FIGS. 5A-5C. In each of the examples, fluid may flow freely in the direction of arrow 94. However, fluid flow opposite to the direction of arrow 94 will force one-way valve 80 to close, thereby preventing backflow. In order to re-open one-way valve 80, sufficient pressure in the direction of arrow 94 must be provided, thus ensuring that fluid moves only in the correct direction.

As shown in FIG. 5A, one-way valve 80 may comprise orifice plate 82 in series with one-way valve 80, illustratively, duck-bill valve 84. Both orifice plate 82 and duck-bill valve 84 may be mounted within outlet catheter 40 or in the housing of pump 60. Flow in the direction of arrow 94 will open duck-bill valve 84 and permit fluid flow through outlet catheter 40. One-way valve 80 alternatively or additionally may comprise a variety of other flow restrictive elements, such as a multiple orifice plate, a filter element, or any other discrete element or combination of elements that can provide a flow resistance capable of yielding the flow rates described herein.

FIG. 5B depicts another one-way valve 80 comprising orifice plate 82 in series with umbrella valve 86. Umbrella valve 86 includes an elastomeric membrane 88 that opens under pressure to permit flow in the direction of arrow 94.

FIG. 5C depicts yet another one-way valve 80 comprising spring-loaded ball valve 90 disposed in valve seat 92. Valve seat 92 also serves as an orifice to limit flow through the assembly and control the direction of the fluid flow. Flow in direction of arrow 94 will open ball valve 90 and permit flow through the orifice defined by valve seat 92.

In the above cases, the orifice may be selected to provide a desired flow rate when the patient is in a vertical position. One-way valve 80 will be implanted within the patient with a known orientation, usually vertical, in order to provide a known pressure head of CSF onto orifice 82 or 92. This pressure will be sufficient to open the associated one-way valve 80 and flow will be established when the patient is in an upright position. Suitable orifice diameters in the range from 0.03 mm to 0.4 mm, preferably from 0.1 mm to 0.2 mm, for orifices having a thickness in the range from 0.001 mm to 100 mm, preferably from 1 mm to 5 mm, in order to establish average hourly flow rates in the range from 0.5 ml/hour to 15 ml/hour, preferably 1 ml/hour to 3 ml/hour.

Figure 6:
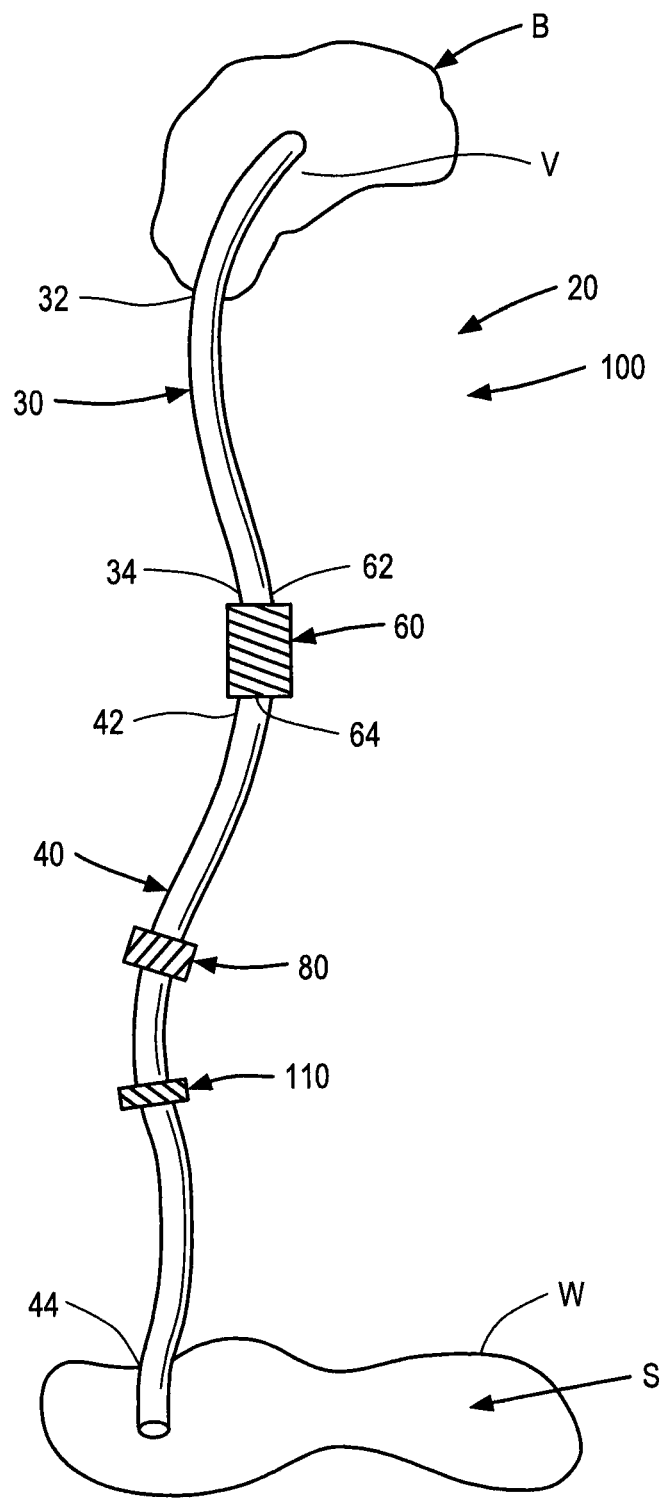
FIG. 6 is a schematic view of the implantable components connected to a brain and a stomach.

Referring to FIG. 6, outlet catheter 40 further may include bacterial filter 110 between inlet end 42 and outlet end 44 to prevent bacteria from migrating backward through the system 20 to the patient's brain. Although one-way valve 80 is located along outlet catheter 40, bacterial filter 110 may be desirable to further prevent bacteria from reaching the brain in the event of malfunction of pump 60, e.g., if pump 60 should become clogged or inoperable. As depicted in FIG. 2, bacterial filter 110 may be incorporated in the housing of pump 60, and may include ultraviolet ("UV") light module 112 configured to irradiate the CSF and destroy bacteria passing within outlet catheter 40. Optionally, bacterial filter 110 may be replaced by antibiotic or antimicrobial coatings disposed on or impregnated within some or all of the components of system 20.

In accordance with the principles of the present invention, it is believed that CSF that reaches the stomach will be broken down by the hydrochloric acid that is naturally present in gastric acid, thereby neutralizing particles, such as BA and tau, within the CSF. The CSF, along with the unwanted and broken down particles, will be excreted through the normal digestive tract of the patient. Alternatively, if the CSF is transferred to the bladder it may be excreted, thereby ridding the body of harmful particles.

Figure 7:
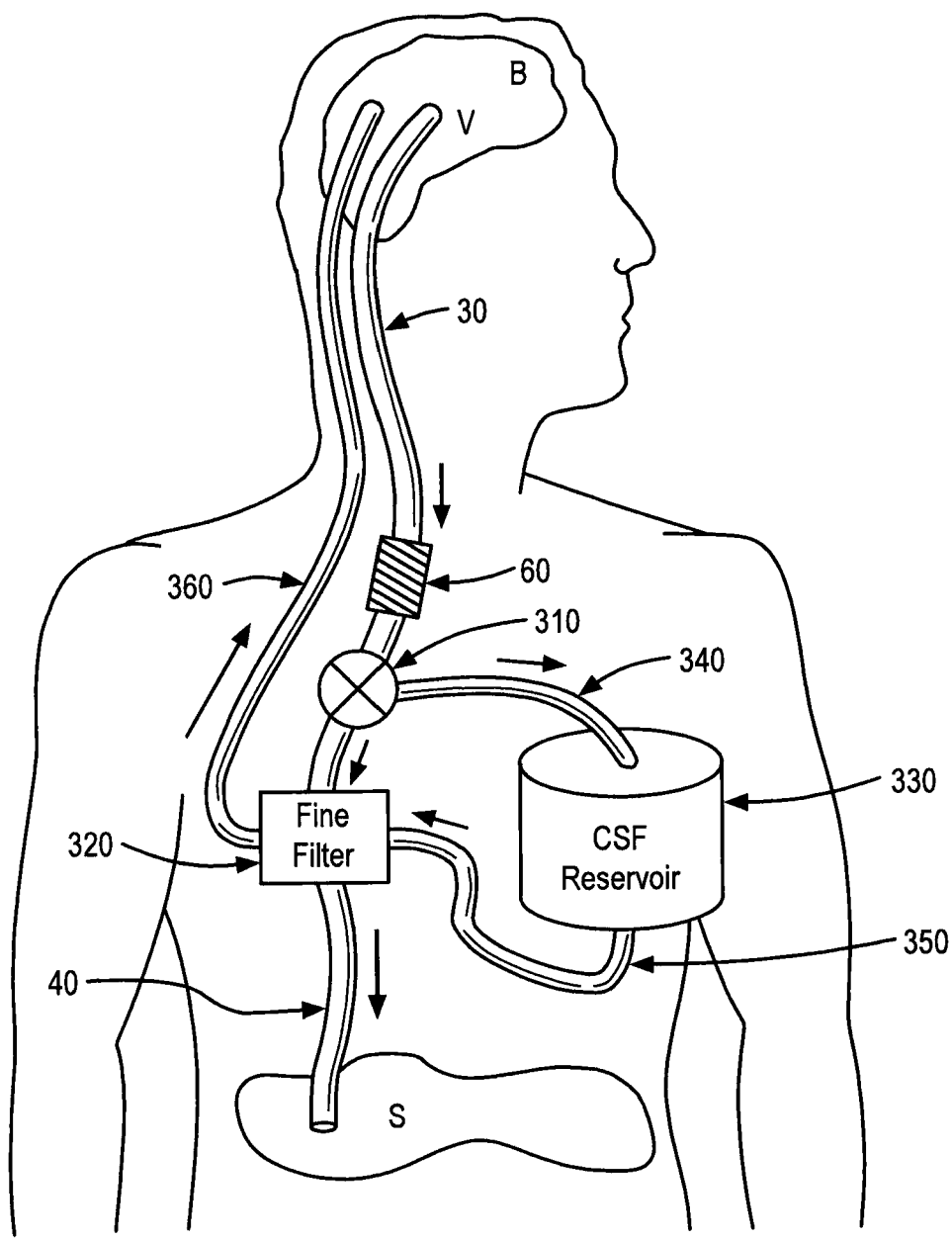
FIG. 7 is a schematic diagram of a fluid moving and circulating system with one filter.

Referring to FIG. 7, exemplary embodiment of a system in accordance with the principles of the present invention comprises implantable pump 60, valve 310, inlet catheter 30, return catheter 360, outlet catheter 40, fine filter 320, and CSF reservoir 330. Inlet catheter 30 is configured to connect the CSF within a cerebral ventricle V of a patient to pump 60. Return catheter 360 is configured to connect fine filter 320 to cerebral ventricle V or spine of the patient. Outlet catheter 40 is configured to connect fine filter 320 to stomach S or bladder of the patient. Inlet catheter 30, return catheter 360, and outlet catheter 40 may be sealed to cerebral ventricle V and/or stomach S or bladder wall with a flange. Pump 60, which in a preferred embodiment may be a positive displacement gear pump, may be located in the chest or abdomen of the patient, and is configured to transfer fluid from inlet catheter 30 to return catheter 360 or outlet catheter 40. Valve 310 is configured to direct the CSF towards fine filter 320 or CSF reservoir 330. Fine filter 320 is configured to trap the harmful particles in the CSF and transport the filtered CSF to return catheter 360. CSF reservoir 330 stores CSF, which is used to wash the trapped particles off fine filter 320 and carry them to stomach S or bladder of the patient.

In some embodiments as illustrated in FIG. 7, pump 60 drains CSF from brain B through inlet catheter 30. The drained CSF passes through valve 310 and enters fine filter 320 during normal operation. Fine filter 320 may have pores that can trap all particles in the CSF with molecular weights greater than, for example, 4 kDa. The filtered CSF is then directed to return catheter 360, which transports the filtered CSF back to brain B to replenish the CSF in brain B, thus reducing the concentration of the harmful particles in the CSF, promoting dissolution of existing plaques, and keeping the volume and pressure of the CSF in brain B at a relatively stable level.

During normal operation, particles trapped by filter 320 accumulate at the inlet of fine filter 320 and gradually block the flow of the CSF. When fine filter 320 is blocked by the trapped particles, the pressure at the inlet of fine filter 320 increases, which causes valve 310 to change direction of the CSF flow towards CSF reservoir 330 through bypass catheter 340. CSF stored in CSF reservoir 330, along with CSF redirected by valve 310, is transferred to fine filter 320 to wash the trapped particles off fine filter 320. The CSF carries the particles washed off fine filter 320 towards stomach S or bladder of the patient through outlet catheter 40 as disclosed above. After the trapped particles are washed off fine filter 320, the pressure at the inlet of fine filter 320 is reduced, and the system goes back to normal operation where valve 310 directs the CSF flow from pump 60 towards fine filter 320, which filters the CSF and send the filtered CSF back to brain B through return catheter 360.

CSF in CSF reservoir 330 may be stored by redirecting the CSF flow towards CSF reservoir 330 periodically. It also may be stored as the pressure at the inlet of fine filter 320 reaches a predetermined level. Alternatively, CSF reservoir 330 may be filled with liquid, such as sterile isotonic saline solution, from a source external to the body of the patient.

In the above example as illustrated by FIG. 7, particles with molecular weights greater than 60 kDa are blocked by fine filter 320 with other particles whose molecular weights are between 4 kDa and 60 kDa. In some embodiments, it may be desirable to circulate particles with molecular weights greater than 60 kDa back to the brain of the patient as these particles may not be neurotoxic or may not contribute to the onset of Alzheimer's disease.

Figure 8:
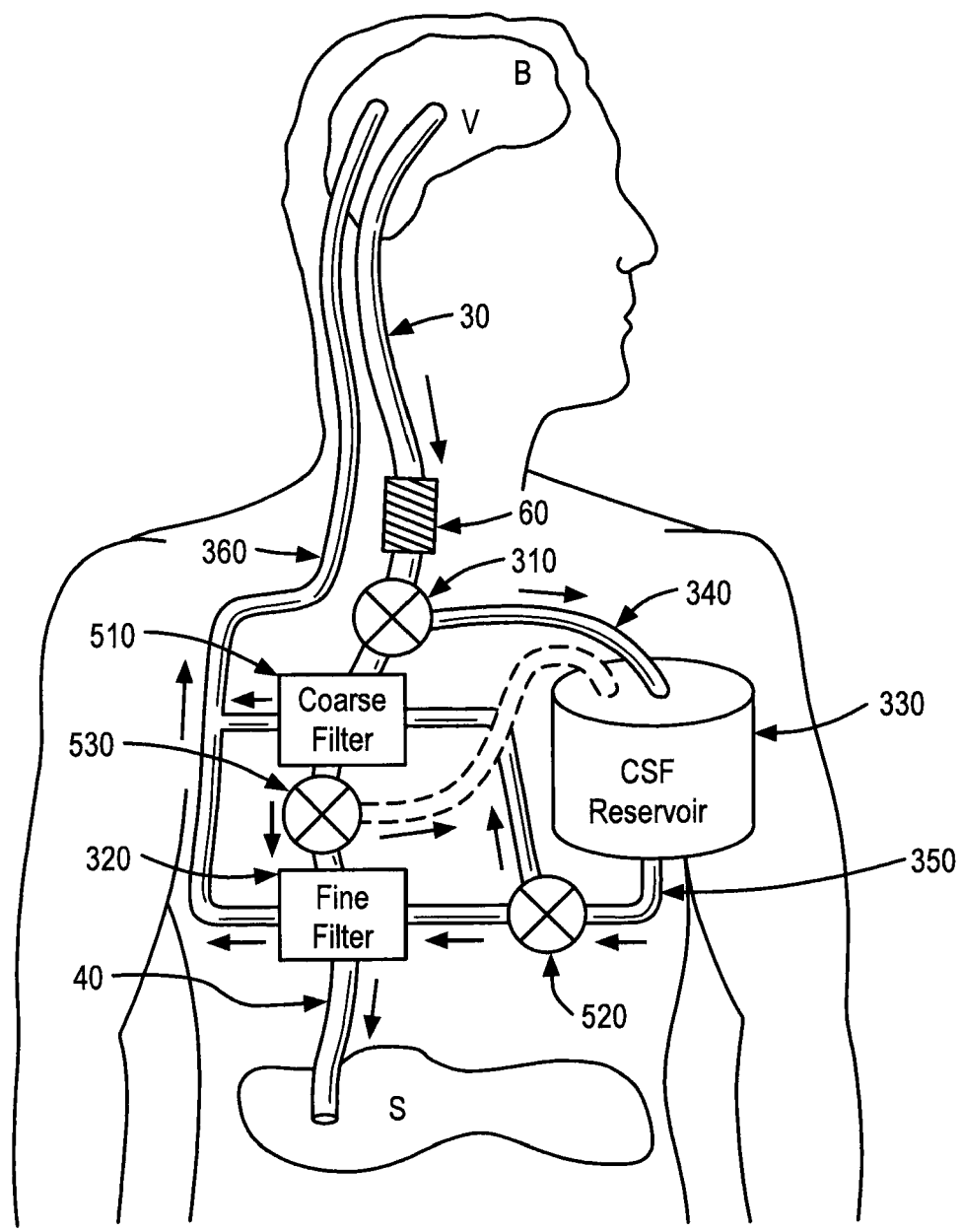
FIG. 8 is a schematic diagram of a fluid moving and circulating system with two filters.

In some embodiments as illustrated in FIG. 8, the system may comprise two or more filters in serial on the path of the circulation of the CSF. Coarse filer 510 may have pores that can block particles with molecular weights greater than, for example, 60 kDa; fine filter 320 may have pores that can block particles with molecular weights greater than, for example, 4 kDa, such as Aβ42 oligomers. During normal operation, CSF drained out of brain B by pump 60 is directed to coarse filter 510 through valve 310. Particles with molecular weights greater than 60 kDa are trapped by coarse filter 510 and accumulate at the inlet of coarse filter 510. The filtrate is then directed to fine filter 320 through valve 530. Fine filter 320 blocks particles with molecular weights greater than 4 kDa.

The filtrate from fine filter 320 is then transported back to brain B through return catheter 360.

When the particles accumulate at fine filter 320 and coarse filter 510, the flow of the CSF is blocked and the pressures of the CSF at the inlets of fine filter 320 and coarse filter 510 increase. The increased pressure causes valves 310 and/or 530 to change the direction of the CSF flow towards CSF reservoir 330, and triggers the rinsing of the corresponding filter. For example, when the CSF pressure at coarse filter 510 reaches a threshold limit, valve 310 redirects the CSF flow towards CSF reservoir 330. Valve 520 is also activated to transfer the CSF from CSF reservoir 330 to coarse filter 510. The CSF rinses coarse filter 510, and carries the particles with molecular weights greater than 60 kDa that are washed off coarse filter 510 back to brain B through return catheter 360.

Similarly, when fine filter 320 is blocked by particles with molecular weights between 4 kDa and 60 kDa, valve 520 is activated to transfer the CSF form CSF reservoir 330 to fine filter 320. The CSF from CSF reservoir 330 washes the trapped particles that have molecular weights between 4 kDa and 60 kDa off fine filter 320 and carries these harmful particles to stomach S or bladder of the patient through outlet catheter 40.

In a preferred embodiment, inlet catheter 30, outlet catheter 40, return catheter 360, pump 60, CSF reservoir 330, and the valves and filters are implanted separately and then coupled together. In an alternative embodiment, one or more of inlet catheter 30, outlet catheter 40, return catheter 360, pump 60, CSF reservoir, and the valves and filters may be coupled together prior to implantation and implanted together.

One-way valve as described above also may be positioned along inlet catheter 30, outlet catheter 40, or return catheter 360 to provide unidirectional flow of CSF within the catheters.

The systems as illustrated in FIGS. 7 and 8 may use filters of different pore sizes from the ones described above to block harmful particles while retaining nontoxic particles. The systems as illustrated in FIGS. 7 and 8 further may include similar bacterial filters, pressure sensors, or flow sensors as described above.

Referring again to FIG. 2, system 20 may include extracorporeal controller 200 that communicates wirelessly with implantable components 100. Extracorporeal controller 200 may provide power to the implantable components and/or control activation of the implantable components, such as pump 60.

Implantable components 100 may be powered by battery 70, or alternatively by a super-capacitor, or other energy storage device. In a preferred embodiment, the power/energy source may be rechargeable. For example, battery 70 may be coupled to implantable inductive charging circuit 72 configured to receive energy from inductive energy transmission circuit 202 of extracorporeal controller 200.

Microcontroller 120 may be coupled to a first transceiver, such as radio frequency (RF) wireless transceiver 122. Extracorporeal controller 200 may be coupled to a second transceiver, such as RF transceiver 222. RF wireless transceiver 122 and RF transceiver 222 may bi-directionally communicate information, such as the operation of the pump, the CSF pressure, the desired drainage rate of the CSF. For example, microcontroller 120 may receive programmed instructions from extracorporeal controller 200 relating to pump activation intervals, targeted volumes of CSF to be pumped and desired flow rates. Additionally, extracorporeal controller 200 may receive data or information from microcontroller 120 relating to pump activation periods, measured pressures, and actual volumes of CSF pumped through inlet catheter 30, return catheter 360, or outlet catheter 40.

Extracorporeal controller 200 preferably includes processor 220 to coordinate and control its various components and functions. Extracorporeal controller 200 further may include power source 224 to power the extracorporeal controller (and potentially also implantable components 100), and may comprise a battery or an electrical outlet. Extracorporeal controller 200 further may include memory 226 to record information, such as the information received from implantable components 100 or a specific algorithm to convey to the implantable components regarding the drainage of the CSF from the brain.

In order for the patient or the physician to enter information into system 20 or for system 20 to display information, extracorporeal controller 200 preferably includes input/display device 230 and/or port 232 to connect to computer 234, such as a laptop computer. Input/display device 230 may include indicators or a control interface to control system 20 and display detailed information about the system. Extracorporeal controller 200 optionally may wirelessly convey or receive information from computer 234, such as whether system 20 is properly functioning, the current (and past) CSF pressures, the volume of CSF drained, the current (and past) flow rate of the CSF through the system, and/or whether pump 60 is currently activated. This information may be conveyed to the patient or physician as a visual message or indicator signal, such as a light or audible signal, that is initiated once pump 60 has been activated. Computer 234 may optionally provide power to extracorporeal controller 200.

Modification of the above-described methods for carrying out the invention, and variation of the mechanical aspects of the invention that are obvious to those of skill in the arts are intended to be within the scope of the claims. Moreover, various combinations of aspects between examples are also contemplated and are considered to be within the scope of this disclosure.

What is claimed is:

1. An apparatus for removing particles contributing to onset of Alzheimer's disease from a patient, comprising:
   an implantable pump having an inlet port and an outlet port;
   an inlet catheter having an inlet end and an outlet end, the inlet end configured to be disposed in fluid communication with a source of cerebrospinal fluid, and the outlet end coupled to the inlet port of the implantable pump;
   an outlet catheter having an inlet end and an outlet end, the inlet end in fluid communication with the outlet port of the implantable pump, and the outlet end configured to be disposed through a stomach or bladder wall of the patient;
   a fine filter in fluid communication with the implantable pump through the output port of the implantable pump, the fine filter configured to block the particles contributing to onset of Alzheimer's disease;
   a return catheter having an inlet end coupled to the fine filter, and an outlet end configured to be disposed in fluid communication with a different area in the source of cerebrospinal fluid; and
   a reservoir in fluid communication with the fine filter, wherein the reservoir contains cerebrospinal fluid for washing the fine filter,
   wherein the inlet end of the outlet catheter is in fluid communication with the output port of the implantable pump through the fine filter.

2. The apparatus of claim 1, further comprising:
   a one-way valve disposed between the inlet end of the inlet catheter and the outlet end of the outlet catheter, the one-way valve configured to permit cerebrospinal fluid to flow only from the inlet catheter to the outlet catheter.

3. The apparatus of claim 1, further comprising a bacterial filter disposed between the inlet end of the inlet catheter and the outlet end of the outlet catheter.

4. The apparatus of claim 3, further comprising an ultraviolet light module disposed between the inlet end of the inlet catheter and the outlet end of the outlet catheter and configured to irradiate fluid passing through the outlet catheter.

5. The apparatus of claim 1, further comprising a microcontroller that controls operation of the implantable pump.

6. The apparatus of claim 5, further comprising a pressure sensor disposed in communication with the inlet catheter to monitor pressure of the cerebrospinal fluid at the inlet end of the inlet catheter, wherein the microcontroller activates the implantable pump responsive to an output of the pressure sensor.

7. The apparatus of claim 5, further comprising a flow sensor disposed in communication with the inlet catheter to monitor at least one of volume and flow rate of cerebrospinal fluid passing through the inlet catheter, wherein the microcontroller controls the implantable pump responsive to an output of the flow sensor.

8. The apparatus of claim 5, wherein the microcontroller includes a clock, and further is programmed to activate the implantable pump periodically responsive to the clock to pump a predetermined amount of cerebrospinal fluid from the source of cerebrospinal fluid to the stomach or bladder.

9. The apparatus of claim 1, further comprising:
   a battery coupled to the implantable pump; and
   an implantable inductive charging circuit coupled to the battery.

10. The apparatus of claim 9, further comprising an extracorporeal controller, the controller including an inductive energy transmission circuit configured to transmit energy to the implantable inductive charging circuit.

11. The apparatus of claim 10, wherein the microcontroller is coupled to a first transceiver and the controller is coupled to a second transceiver, and the first and second transceivers communicate information relating to at least one of operation of the implantable pump and status of the apparatus.

12. The apparatus of claim 1, further comprising a valve in fluid communication with the implantable pump, the fine filter, and the reservoir, wherein the valve is configured to transport cerebrospinal fluid from the implantable pump to at least one of the fine filter and the reservoir.

13. The apparatus of claim 1, further comprising a coarse filter disposed between the implantable pump and the fine filter, wherein:
   the coarse filter is configured to block particles larger than the particles contributing to onset of Alzheimer's disease in the cerebrospinal fluid from the implantable pump, and transport the filtered cerebrospinal fluid to the fine filter; and
   the coarse filter is in fluid communication with the reservoir and the return catheter such that the cerebrospinal fluid contained in the reservoir may wash the particles larger than the particles contributing to onset of Alzheimer's disease off the coarse filter and carry the particles to the return catheter for returning to the different area in the source of cerebrospinal fluid.

14. The apparatus of claim 13, further comprising a valve in fluid communication with the reservoir, the fine filter, and the coarse filter, wherein the valve is configured to transport the cerebrospinal fluid contained in the reservoir to at least one of the fine filter and the coarse filter.

15. A method for reducing concentration of particles contributing to onset of Alzheimer's disease in a patient's brain, comprising:
providing an inlet catheter coupled to an implantable pump;
providing an outlet catheter in fluid communication with the implantable pump;
providing a fine filter in fluid communication with the implantable pump, the fine filter configured to block the particles contributing to onset of Alzheimer's disease;
providing a return catheter coupled to the fine filter;
coupling the inlet catheter to a source of cerebrospinal fluid within the patient;
coupling the outlet catheter to at least one of the patient's stomach and bladder;
coupling the return catheter to a different area in the source of cerebrospinal fluid within the patient; and
activating the implantable pump to pump at least a portion of cerebrospinal fluid from the source of cerebrospinal fluid to the patient's stomach or bladder while preventing backflow of the cerebrospinal fluid to the source of cerebrospinal fluid, to pump at least a portion of cerebrospinal fluid from the source of cerebrospinal fluid to the fine filter via the inlet catheter, and to transport cerebrospinal fluid from the fine filter to the different area in the source of cerebrospinal fluid via the return catheter.

16. The method of claim 15, further comprising:
providing a microcontroller configured to control operation of the implantable pump; and
activating the implantable pump via the microcontroller.

17. The method of claim 15, further comprising:
providing a reservoir storing cerebrospinal fluid and in fluid communication with the fine filter;
coupling the outlet catheter to the fine filter such that the output catheter is in fluid communication with the implantable pump through the fine filter;
rinsing the fine filter with the cerebrospinal fluid stored in the reservoir; and
transporting the cerebrospinal fluid rinsing the fine filter to at least one of the patient's stomach and bladder via the outlet catheter.

18. The method of claim 17, further comprising:
positioning a coarse filter between the implantable pump and the fine filter such that the coarse filter is in fluid communication with the implantable pump and the fine filter;
filtering the at least a portion of cerebrospinal fluid pumped from the source of cerebrospinal fluid using the coarse filter; and
transporting the filtered cerebrospinal fluid to the fine filter.

19. The method of claim 18, further comprising:
coupling the coarse filter to the return catheter;
connecting the coarse filter with the reservoir such that the coarse filter is in fluid communication with the reservoir;
rinsing the coarse filter with the cerebrospinal fluid stored in the reservoir; and
transporting the cerebrospinal fluid rinsing the coarse filter to the return catheter for returning to the different area in the source of cerebrospinal fluid.

20. The method of claim 15, further comprising:
providing a battery coupled to the implantable pump, the battery further coupled to an implantable inductive charging circuit;
providing an extracorporeal controller, the controller including an inductive energy transmission circuit configured to transmit energy to the implantable inductive charging circuit; and
transmitting energy to the implantable inductive charging circuit via the controller to power the implantable pump.

* * * * *